(12) United States Patent
Dhawan et al.

(10) Patent No.: US 6,534,696 B1
(45) Date of Patent: Mar. 18, 2003

(54) METHOD OF PRODUCING A POPPY PLANT

(75) Inventors: Om Parkash Dhawan, Lucknow (IN);
Saba Shahabuddin, Lucknow (IN);
Mala Trivedi, Lucknow (IN); Abdul Sattar, Lucknow (IN); Mansoor Alam, Lucknow (IN); Abdul Samad, Lucknow (IN); Mohammad Zaim, Lucknow (IN); Samresh Dwivedi, Lucknow (IN); Surendra Pratap Singh, Lucknow (IN); Hemendra Pratap Singh, Lucknow (IN); Suman Preet Singh Khanuja, Lucknow (IN); Mahendra Pandurang Darokar, Lucknow (IN); Ajit Kumar Shasney, Lucknow (IN); Madan Mohan Gupta, Lucknow (IN); Rajesh Luthra, Lucknow (IN); Jawahar Ram Sharma, Lucknow (IN); Raj Kishori Lal, Lucknow (IN); Hari Om Misra, Lucknow (IN); Alok Kalra, Lucknow (IN); Sushil Kumar, Lucknow (IN)

(73) Assignee: Council of Scientific and Industrial Research, New Delhi (IN)

(*) Notice: Subject to any disclaimer, the term of this patent is extended or adjusted under 35 U.S.C. 154(b) by 0 days.

(21) Appl. No.: 09/537,186

(22) Filed: Mar. 29, 2000

(51) Int. Cl.$^7$ ................................................. A01H 5/00
(52) U.S. Cl. ........................ 800/298; 800/323; 800/265
(58) Field of Search ................................. 800/323, 298, 800/265

Primary Examiner—Bruce R. Campell
Assistant Examiner—Annette H. Para
(74) Attorney, Agent, or Firm—Sughrue Mion, PLLC

(57) ABSTRACT

The invention relates to a disease resistant and high yielding variety of opium poppy plant (*Papaver somniferum* L. 2n=22) christened as 'Rakshit'.

11 Claims, 3 Drawing Sheets

(2 of 3 Drawing Sheet(s) Filed in Color)

Figure 1

A single plant of the disease resistant and high yielding variety 'Rakshit' of opium poppy

Figure 2

A field view of the variety 'Rakshit' of opium poppy

Figure 3

Typical RAPD profile of Rakshit (*Papaver sominiferum*)

Lane M : DNA Marker I Eco RI + Hind III
Lane 1 : AAATCGGAGC      Lane 2 : GTCCTACTCG
Lane 3 : TGCGCGATCG      Lane 4 : AACGTACGCG
Lane 5 : GCACGCCGGA      Lane 6 : CGGGATCCGC
Lane 7 : GCGAATTCCG      Lane 8 : CCCTGCAGGC
Lane 9 : AAGATAGCGG      Lane 10 : GGATCTGAAC
Lane 11 : TTGTCTCAGG     Lane 12 : CATCCCGAAC
Lane 13 : GGACTCCACG     Lane 14 : AGCCTGACGC

METHOD OF PRODUCING A POPPY PLANT

FIELD

The present invention relates to the development of a disease resistant and high yielding variety of opium poppy plant (*Papaver somniferum* L. 2n=22) christened as 'Rakshit'. More particularly, the invention relates to the development of a high seed and straw yielding (concentrated poppy straw) variety of opium poppy by hybridizing the highly resistant sources in the germplasm with high yielding lines/genotypes followed by repeated selection and evaluation for the said characters for six years under natural and artificial epiphytotic conditions. The resultant variety is highly resistant to the most destructive disease, downy mildew caused by *Peronospora arborescens* (Berk) de Barry and moderately resistant to both damping off caused by *Pythium dissotocum* Drechsler and collar rot caused by *Rhizoctonia solani* Kuhn. The variety being highly self pollinated is distinct, uniform and stable and suitable for commercial cultivation.

BACKGROUND OF THE INVENTION

Opium poppy is commercially cultivated in a large number of countries under strict vigilance. International Narcotic Control Board (INCB) Vienna, regulates the opium poppy cultivation in the world. The latex obtained by the incision of unripe capsules is known as opium which is the source of several pharmacologically important alkaloids. Morphine, codeine, thebaine, narcotine and papaverine are the most important alkaloids produced by the plant and are exploited by the pharmaceutical industry as analgesics, antitussive and antispasmodic. The total world area of illicit cultivation of poppy for opium production was about 37000–56000 ha from 1989–1993 according to the INCB, Vienna. Eight to ten thousand tones of opium is produced in India yearly (Bryant, R J, Chemistry and Industry. 7:146–153,1988). This amount of opium covers about half of the world's annual morphine demand. India remains the only country in which the cultivation of opium poppy for gum is still legal. However, the importance of poppy straw has been increasing continuously and world area of poppy cultivation for purposes other than opium production was as large as 25,000–40,000 ha in the early 1990s which increased to 80,000 ha in 1994. This means that the cultivation of poppy for straw is 2–3 times more than that of the area used for licit opium production. Poppy straw and straw concentrate are more important than opium in the production of morphine. More than 50% of the world's morphine is now manufactured from these raw materials. However, the single method of using dry capsules for direct extraction is practiced only in some central European countries. The United Kingdom is the largest producer of morphine from straw concentrate. Australia produced 36,082 kg. of morphine from concentrate in 1993 (INCB,1993). Countries like USA, Spain, South Africa, Norway, Netherlands and Italy import straw concentrate for morphine extraction. Turkey has its own poppy cultivation industry.

Poppy seeds are rich in protein and minerals and are widely used in the food industry. These are also considered to have aphrodisiac and constipating properties (Nerglz and Otles, J. Sci. Food Agr. 66:117, 1994). Anticarcinogenic properties have also been reported in the poppy seeds (Aruna, Food Chem. Toxicol. 30: 11, 1992; Berger, Berger's Medicinal Chemistry, Part II, A. Willey Interscience Publication, 1140, 1979). The seeds contain a high proportion of edible vegetable oil which is rich in unsaturated fatty acids, particularly oleic acid and linoleic acid (Wealth of India—Raw materials vol. 7: 234, 246, 1966). Linolinic acid tends to lower down the blood cholesterol in human beings (cf. Singh et al, Indian J. Agric. Sci. 60: 358, 1990). The biological value if poppy seed oil was found in similar to those of sunflower oil and olive and was considered to be promising for human consumption (Beare et al Nutrition and Metabolism, 23:335–346, 1979). Several other uses of poppy seed and oil have been reported by Teteyl (Tetely, Hort. Rev., 19: 373, 1997).

Opium poppy is attacked by many diseases like downy mildew, damping off, capsule rot, collar rot, stem rot, mosaic etc. which cause huge damage to seed and latex yield. Downy mildew caused by *Peronospora arborescens* is the most destructive and wide spread disease which spreads very rapidly under low temperature and high humidity conditions leading to severe damage to the crop (Kothari and Prasad, Indian Phytopath. 23: 6740–688,1978). Damping off caused by *Pythium dissotocum* occurs most frequently during misty weather when high moisture regime prevails for 7–10 days during the month of January. The disease spreads rapidly and kills large population of the young seedlings in severely infected fields within 15–20 days of its appearance (Alam et al, 1995, Indian Phytopathology 49: 94–97). The collar rot disease caused by *Rhizoctonia solani* appears on young plants of 10–12 fully expanded leaf stage. The infection initally appears as dark brown necrotic lesions at the collar region (a joint between the stem and root) which later turns black resulting in premature death of the infected plants.

All existing varieties of opium poppy at CIMAP (Central Institute of Medicinal and Aromatic Plants), Lucknow, India are highly susceptible to all these diseases and till now no disease resistant and high yielding genotype is available. Hence, there is a strong and pronounced need for disease—resistant poppy varieties. Keeping this objective in view, planned experiments were carried out at CIMAP, Lucknow for developing disease resistant genotypes with high yield potential. The available germplasms were screened for disease resistance and highly resistant sources were identified against all the devastating diseases of opium poppy. These resistant sources were then hybridized systematically with high yielding genotypes followed by repeated selection for the desirable characters in the advanced generations under natural as well as artificial epiphytotic conditions.

OBJECTS

The main object of the invention is to develop poppy varieties resistant to common destructive diseases like downy mildew, damping off, capsule rot, collar rot, stem rot, mosaic etc.

Another object is to develop poppy varieties having high straw and seed yielding capacity.

Yet another object is to provide poppy plants having high morphine content in the straw.

Still another object is to develop poppy plants capable of growing in natural and epiphytotic conditions.

SUMMARY

In accordance with the above and other objectives, the invention provides a novel variety of poppy plant, christened as 'Rakshit', said variety being resistant to common disease like downy mildew damping off, capsule rot, collar rot, stem rot, etc. The said variety 'Rakshit' has high straw and seed yielding capacity as compared to conventional poppy varieties. The straw of the variety is also rich in morphine content.

DETAILED DESCRIPTION

Accordingly, the invention provides a novel disease resistant variety of opium poppy (*Papaver somniferum*) called Rakshit. This variety has yielding capacity and has high speed and straw with high morphine content in the poppy straw. The seeds of the Rakshit plant are deposited at National Gene Bank of Medicinal and Aromatic Plants at Central Institute of Medicinal and Aromatic Plants (CIMAP), Lucknow, India. The Accession Number is CIMAP/IPMC 99/T-7 (CIMAP 0518). The seeds of this Rakshit plant were also deposited at National Collections of Industrial and Marine Bacteria Limited (NCIMB), 23 St. Macher Drive, Aberdeen, United Kingdom on Sep. 12, 2002. The Accession No. is NCPAT17699 (NCIMB 41148).

Accordingly, the present invention provides a disease resistant and high yielding variety Rakshit of opium poppy (*Papaver somniferum*) having the following morphological/agronomic features.

| | |
|---|---|
| Plant height | 106–112 cm |
| Peduncle length | 22–26 cm |
| Peduncle colour | green |
| Seed yield | 12–14 q/ha |
| Straw yield | 9–11 q/ha |
| Days to 50% flowering | 90–100 days |
| Days to maturity | 128–134 days |
| No. of capsules/plant | 1–4 |
| No. of stigmatic rays/capsule | 16–18 |
| Latex colour | dark pink |
| No.of seeds/g (seed count/g) | 3350–3390 |
| Seed colour | cream |
| Seed shape | reniform |
| Seed size (L × W) | 1000 × 840–1050 × 855($\mu$m) |
| Leaf area | 127–135 cm$^2$ |
| Pollen fertility | 90–95% |
| Seed germination | 90–98% |
| Oil content in seed | 46–52% |
| Total seed proteins | 28–32% |
| Chlorophyll content | 1.80–1.90 (mg/g fresh weight) |
| Capsule shape | oblong |
| Capsule surface | waxy |
| Leaf colour (based on RHS cards) | 137 B-137C |

(RHS—Royal Horticulture society, London, UK.)

The invention further provides a disease resistant and high yielding variety poppy called 'Rakshit'exhibiting reactions to various diseases as under:

| Disease | Disease rating | Category | Scale used |
|---|---|---|---|
| 1. Downy mildew caused by *Peronospora arborescens* | 1–2 | resistant | (0–9) |
| 2. Damping off caused by *Pythium dissotocum* | 1–2 | tolerant | (0–4) |
| 3. Collar rot caused by *Rhizoctonia solani* | 1–2 | tolerant | (0–4) |

The invention further provides a disease resistant and high yielding variety Rakshit of opium poppy with the following chemical features in the concentrated poppy straw (cps).

| | |
|---|---|
| Morphine | 0.65–0.87% |
| Thebaine | 0.03–0.06% |
| Codeine | 0.15–0.19% |
| Papaverine | 0.02–0.10% |
| Narcotine | 0.12–0.17% |

In an embodiment of the invention the parental material of the said variety Rakshit comprised of IS-22 as the female parent and N-3 as male parent wherein IS-22 was selected on the basis of seed yield and good plant type but was susceptible to downy mildew (DM) and damping off and N-3 was selected on the basis of highly resistant DM reactions.

In another embodiment 0–9 scale disease rating was used for scoring downy mildew reactions under epiphytotic as well as natural field conditions wherein 0–3 was considered resistant (0=no visible disease reactions; 3=less than 20% of the lower leaves covered with disease reactions), 3.1 to 5.0 as tolerant (3.1=more than 20% disease reactions on lower leaves; 5.0=less than 50% disease reactions on lower leaves), 5.1–7.0 as susceptible (5.1=more than 50% disease reactions on all the leaves and stem; 7.0=less than 75% disease reactions on all the leaves and stem) 7.1 to 9.0 as highly susceptible (7.0=more than 75% disease reactions; 9.0=premature death of the infected plant).

In another embodiment of the invention 0–4 scale was used for damping off disease reactions under epiphytotic conditions in the glasshouse wherein 0–1 was considered as resistant (0=no visible reaction, 1=very few minute necrotic lesions of limited growth on the roots, no chlorosis). 1.1–2.0 as tolerant (few necrotic lesions on the roots with chlorotic symptoms only on the lower leaves). 2.1–3.0 as susceptible (many dark brown necrotic lesions on the roots with distinctly visible chlorotic symptoms). 3.1–4.0 as highly susceptible (entire root system with dark brown necrotic and rotting symptoms leading to sudden death of infected seedlings.)

In another embodiment of the invention 0–4 scale disease rating was used for scoring collar rot disease reactions under epiphytotic conditions in the glass house wherein 0–1 was considered resistant (0=no visible reaction; 1=infection restricted up to 1 cm length on the collar region), 1.1–2.0 as tolerant (1.1=infection more than 1 cm length on the collar region, 2.0=infection starts spreading in the root and shoot), 2.1–3.0 as susceptible (2.1=infection spreads downwards (root) & upwards (stem) and yellowing of lower leaves, 3.0=pronounced rotting symptoms start appearing at the collar region as well as on the stem of infected plants.), 3.1–4.0 as highly susceptible (3.1=dark brown rotting become more prominent, 4.0=collar region and stem become pulpy resulting into the toppling of infected plants).

The invention further provides a method for development of disease resistant and high yielding variety of poppy called 'Rakshit' said method comprising the steps of:

a) selecting parental lines wherein one of the parental line is high yielding, but susceptible and another being highly resistant to downy mildew disease, b) hybridizing the high yielding genotypes with resistant genotypes in all possible combinations, c) raising of the F$_2$ generations of all the cross combinations and then selfing only the resistant plants in the F$_2$ progenies to raise the F$_3$ seeds.

d) selection of the highly resistant plants in the F$_3$ generation showing high seed and straw yield.

e) initial evaluation of 286 F$_4$ plant progenies in row trial and selection of seven (T-3, T-7, T-16, T-20-16, T-20-

17, T-79 and T-80) promising plant progenies on the basis of distinctiveness, uniformity, disease rating, seed and straw yield.

(f) screening of the selected plants within the said seven plant progenies for damping off, collar rot and downy mildew under epiphytotic conditions in the glasshouse and under natural conditions in the field.

(g) purification of the selected lines showing high to moderate resistance for all the three diseases in the advanced generation ($F_5$) by selfing only the highly resistant and high seed/straw yielding plants.

(h) bench scale evaluation of the purified lines (T-7,T-20-16, T-20-16, T-79 and T-80) against the released variety Shyama as check (RBD 8 $m^2$ plots, 3 replications, r×r=50 cm)

(i) Pilot scale evaluation of the elite lines (T-7,T-20-16&T-20-17) against high yielding released varieties (Vivek, Sanchita, Shyama, Shubhra, Jawahar-16) for two years for the yield and quality traits.

In an embodiment, the parental materials consisting of high yielding but susceptible genotypes (IS-22, SPS-49, Thailand, Shweta broad, Shyama, Jawahar-16) and the highly resistant sources for the most destructive disease downy mildew (N-3, I-14, and SPS-20) were screened from the germplasm under strict epiphytotic conditions.

In a further embodiment of the invention, the invention further provides a disease resistant and high yielding variety of poppy called "Rakshit" whose seeds were deposited at National Collections of Industrial and Marine Bacteria Limited (NCIMB), 23, St. Macher Drive, Aberdeen, United Kingdom on Sep. 12, 2002, bearing the Accession No. NCPAT17699 (NCIMB 41148) and CIMAP, Lucknow, India, bearing the Accession No. CIMAP/IPMC 99/T-7 (CIMAP 0518).

The invention is described in detail with reference to the following examples which are provided for illustration only and should not be considered as limitations on the inventive concept.

BRIEF DESCRIPTION OF THE DRAWINGS

The patent application file contains at least one drawing executed in color. Copies of this patent or patent application publication with color drawing(s) will be provided by the Office upon request and payment of the necessary fee.

Figure 1:
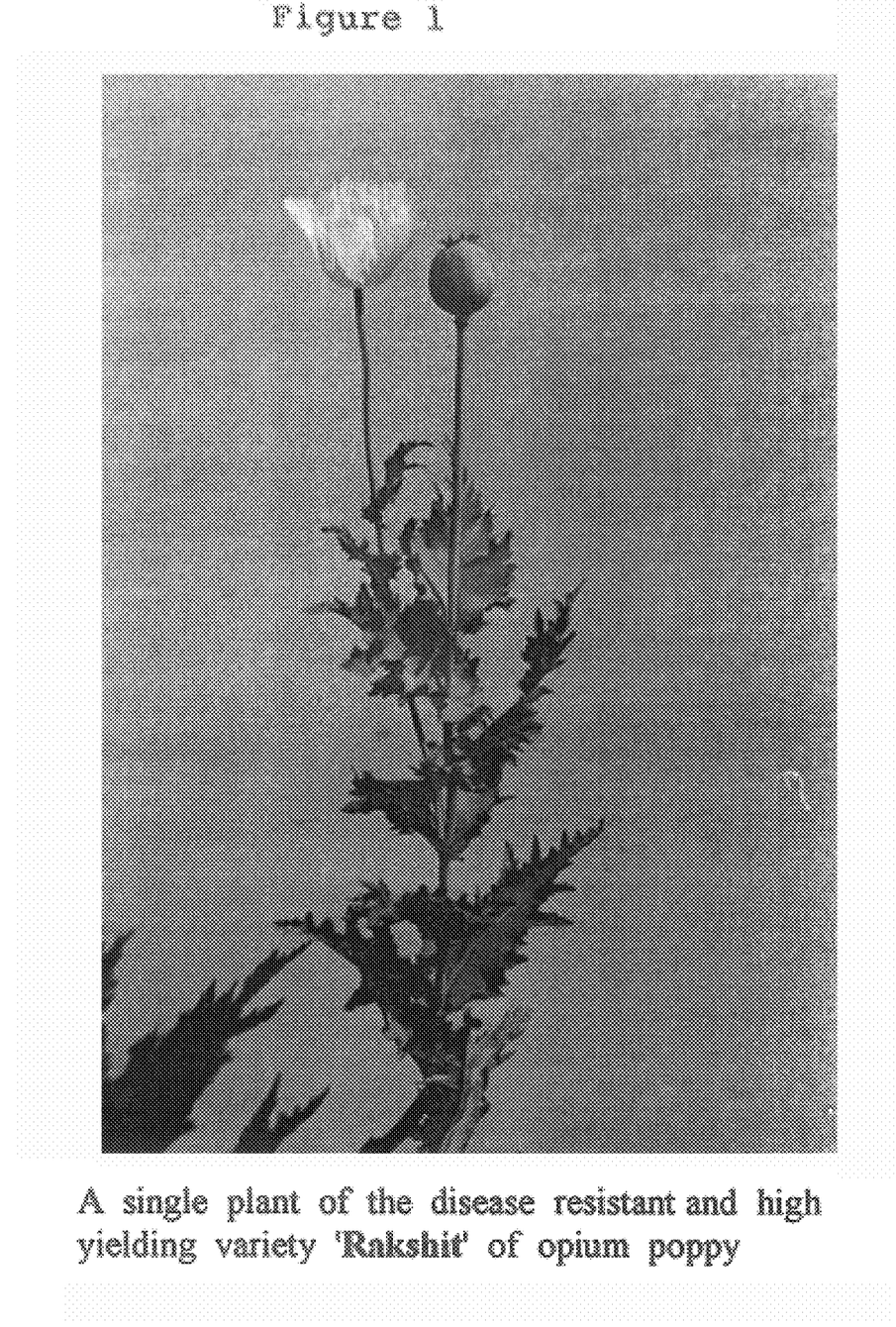
FIG. 1 represents a single 'Rakshit' plant.

The breeding programme for disease resistance in opium poppy was initiated in the year 1989 and germplasm was screened to identify resistance sources for different diseases like downy mildew caused by *Peronospora arborecens,* damping off caused by *Pythium dissotocum,* capsule rot caused *Erwinia carotovora* and mosaic disease caused by poppy mosaic virus POMV-1 (Sattar et al 1995, Curr. Res. on Med. & Arom. Plants 17: 315–320; Sattar et al 1997, J. Med. Arom. Plant Sciences. 19: 11–13). As downy mildew (DM) is the most important and destructive disease of opium poppy, three highly resistant sources (N-3, I-14 and SPS-20) identified during screening of the germplasm accessions were involved in the breeding programme. Other desirable genotypes selected were IS-22, SPS-49, Thailand (on the basis of good plant type and high seed yield) and high yielding released varieties Shewta broad, Shyama & Jawahar-16. Single plant of "Rakshit" is represented in FIG. 1.

Hybridization Programme and Initial Selection

All selected genotypes were hybridized in all possible reciprocal combinations and $F_1$ generation was raised for each individual cross. $F_2$ generation was raised which showed high level of segregation for all the desirable yield traits like seed yield, straw yield and resistance to downy mildew. Only good looking plants showing highly resistant DM reactions were selfed to raise $F_3$ seeds. A large number (approx. 2000) of plants were selected in the $F_3$ generation on the basis of seed and straw yield per plant along with the resistance reactions to DM out of which 286 plants were short listed for evaluation in plant to row trial.

Initial Evaluation Trial

Figure 2:
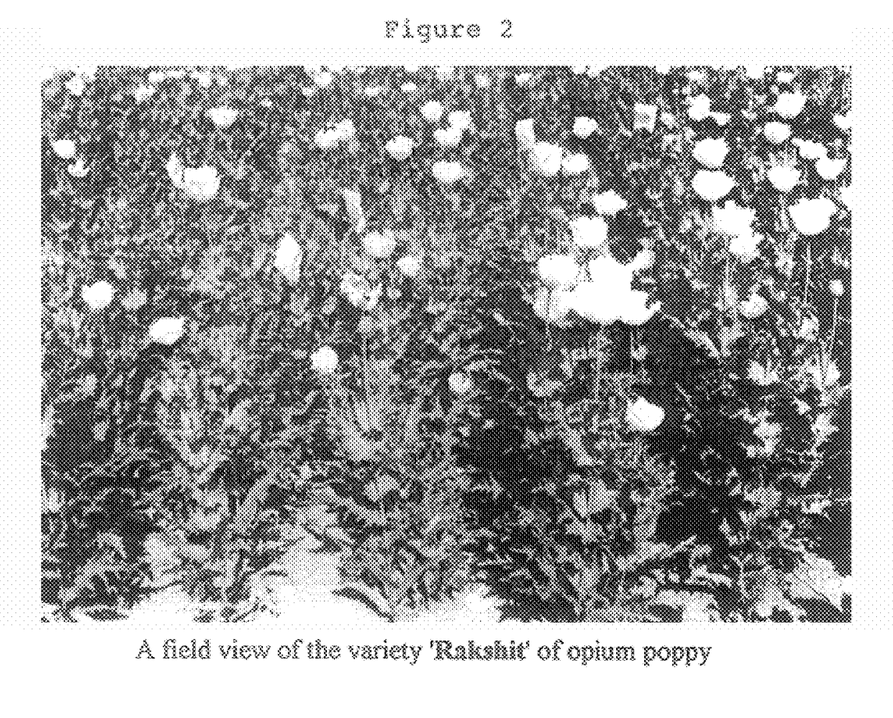
FIG. 2 represents a field view of the plants of the invention.

Initial evaluation trial (RBD, 2 m rows, 2 replications, row×row=50 cms) was layed out during 1993–94 season including 286 $F_4$ plant progenies. The data were collected for yield characteristics and DM reactions. Seven plant progenies were selected (T-3, T-7, T-16, T-20-16, T-79 & T-80) on the basis of distinctiveness, uniformity in highly resistant DM rating, seed and straw yield in all the replications. A large number of promising plants were selfed within these selected lines which were individually carried forward for further evaluation. FIG. 2 is a field view of "Rasshit".

Screening for Multiple Disease Resistance

A large number of selected plants selfed within the said seven selected lines were grown both in pots in the glasshouse and in the field with three replications for screening against three major diseases of opium poppy viz. downy mildew, damping off, and collar rot. While data were collected under natural inoculum conditions in the field for all the three diseases, artificial epiphytotic conditions were created for screening against all the three diseases in the glasshouse.

For screening against damping off, the fresh pathogenic culture of *Pythium dissotocum* (C-80) was multiplied on moist sterilized sand: soil: cornflakes (6:3:1 v/v) mixture in 500 ml Erlenmeyer flasks for 7–10 days at 25° C. The inoculum was then mixed with moist sterilized soil (1:10 V/V) in pots and incubated for 3 days at 20 +2° C. Sowing was carried out in the pots keeping a set of control (without inoculum). The responses were scored at 3 days interval, 15 days after germination using 0–4 scale.

For screening against collar rot disease the inoculum of *Rhizoctonia solani* was maintained on potato-dextrose-agar medium and the inoculations of the mycelium were made on the collar regions of the individual plants which survived screening of damping off at 35 to 40 day old plants. The pots were irrigated after inoculation and were kept in the humidity chamber for 48 hours. The observations were made at two days interval.

For screening against DM inoculum was prepared from the live material as the causal organism, *Peronospora arborescens* is an obligate parasite. The young plants showing severe systemic infection of DM were collected from the opium poppy fields. An aqueous suspension of the inoculum was obtained ($1 \times 10^7$ conidia/ml of sterile distilled water). The surviving plants in the pots showing tolerance to damping off and collar rot were sprayed with conidial suspension on 65 to 70 day old plants and the inoculated pots were kept in a humidity chamber for 48 hours. The data were collected 2–3 weeks after inoculation.

High percentage of plant progenies in the lines T-7, T-20-16 and T-20-17 were found to be highly resistant to DM and moderately resistant to both damping off and collar rot diseases. These plants were individually selfed in the pots and their corresponding progenies were also selfed in the field to raise large number of seeds which were then sown in separate rows during the following season of the year 1995–96 for multiplication of the materials by bagging.

Only highly DM resistant plants showing high seed and straw yield were selfed. The bulked selfed seeds of all the corresponding lines served as basic materials for bench scale and further pilot scale evaluations during the following years (1996–99). The comparison of the variety 'Rakshit' with its parent variety is given in Table 1.

method and T-7 (Rakshit) showed the maximum morphine content in concentrated poppy straw. All the three lines were also highly resistant to DM and moderately resistant to one of the other two diseases (damping off and collar rot). These three elite lines were selected for evaluation in a pilot scale trial during the next season (1997–98).

TABLE 1

Description of the variety Rakshit in comparison to its parents

| | Charecters | Rakshit | IS-22 | N-3 |
|---|---|---|---|---|
| 1 | Plant height (cm) | 109.3 | 110.5 | 100.6 |
| 2 | Peduncle length (cm) | 24.0 | 28.6 | 31.6 |
| 3 | Peduncle colour | green | green | green |
| 4 | Seed yield (q/ha) | 12.59 | 7.62 | 6.41 |
| 5 | Straw yield (q/ha) | 9.55 | 5.02 | 4.44 |
| 6 | Content of chemical constituents in concentrated poppy straw | | | |
| | Morphine | 0.77 | 0.70 | 0.62 |
| | Thebaine | 0.04 | 0.60 | 0.02 |
| | Codiene | 0.17 | 0.15 | 0.16 |
| | Papaverine | 0.06 | 0.08 | 0.02 |
| | Narcotine | 0.15 | 0.12 | 0.17 |
| 7 | Disease score | | | |
| | a. Downy mildew (0–9 scale) | 1.4 | 7.5 | 1.5 |
| | b. Pythium damping off (0–4 scale) | 2.0 | 2.5 | 2.4 |
| | Collar rot (0–4 scale) | 1.6 | 1.0 | 2.8 |
| 8 | Days to 50% flowering | 98.3 | 95.0 | 97.8 |
| 9 | Days to maturity | 132.0 | 123.1 | 128.7 |
| 10 | Number of capsules/plant | 2.0 | 3.2 | 2.1 |
| 11 | Number of stigmatic rays/capsules | 17.7 | 16.5 | 15.1 |
| 12 | Latex colour | dark pink | light pink | pink |
| 13 | Number of seeds/g | 3378 | 3310 | 3290 |
| 14 | Seed colour | cream | cream | cream |
| 15 | Seed shape | reniform | reniform | reniform |
| 16 | Seed size($\mu$m) | 1025 × 847.7 | 950 × 830 | 952 × 825 |
| 17 | Leaf area (cm$^2$) | 128.1 | 118.2 | 123.9 |
| 18 | Pollen fertility(%) | 94.7 | 92.0 | 93.1 |
| 19 | Seed germination (%) | 96.7 | 90.3 | 92.9 |
| 20 | Oil content in seed(%) | 51.60 | 48.2 | 46.8 |
| 21 | Total seed protein | 31.72 | 32.6 | 30.8 |
| 22 | Chlorophyll content (mg/g fresh wt.) | 1.79 | 2.20 | 2.15 |
| 23 | Capsule shape | oblong | oblong | oblong |
| 24 | Capsule surface | waxy | waxy | waxy |
| 25 | Leaf colour (based on RHS) RHS-Royal Horticulture Society, London, UK.) | 137B–137C | 137C–137C | 137B–137C |

EXAMPLE 1

Bench scale trial was laid out during 1996–97 for evaluating the performance of selected seven lines (T-3, T-7 (Rakshit), T-16, T-20-16, T-20-17, T-79, T-80) against their parental genotypes (N-3, I-14,IS-22 and Thailand) and the released varieties (Vivek, Sanchita, Shyama & Jawahar-16) which served as checks. All entries were sown in 8 m$^2$ plots in a randomized block design (RBD) in two replications with row×row distance of 40 cm. The results have been presented in Table -2 which reveals that T-7 (Rakshit), T-20-16 and T-20-17 showed significantly better seed/straw yields in comparison to their parents as well as the released varieties. Morphine content was estimated by HPTLC

EXAMPLE 2

Pilot scale trial was laid out during 1997–98 (RBD, 8 m$^2$ plots, 3 replications, row×row=40 cm) with recently released varieties Shubhra along with other varieties (Vivek, Sanchita, Shyama & Jawahar-16). The results have been presented in Table-3. T-7 (Rakshit) showed 48.8% and 60.5% increase in seed yield over the best checks Vivek and Shubhra, respectively. Similarly T-7 (Rakshit) also recorded 24.7% and 33.3% increase in straw yield over Vivek and Shubhra, respectively. Morphine content was also the highest in T-7 as compared to the best check Shubhra. T-7 (Rakshit) was also found to be highly resistant to DM and tolerant to both damping off and collar rot diseases.

TABLE 2

Performance of the selected lines against their parents and the released varieties during 1996–1997

| Genotypes | Plant height (cm) | Seed yield (g/8 m$^2$) | Straw yield (g/8 m$^2$) | Morphine content (%) | Downy mildew (0–9 scale) | damping off (0–4 scale) | collar rot (0–4 scale) |
|---|---|---|---|---|---|---|---|
| Selected lines | | | | | | | |
| T-3 | 109.5 | 562.3 | 501.9 | 0.69 | 2.5 | 2.5 | 2.6 |
| T-7 (Rakshit) | 105.2 | 810.5 | 707.4 | 0.86 | 1.5 | 1.5 | 1.6 |
| T-16 | 104.2 | 524.9 | 484.2 | 0.70 | 2.4 | 2.5 | 2.2 |
| T-20-16 | 102.1 | 733.2 | 684.5 | 0.75 | 2.0 | 1.6 | 2.1 |
| T-20-17 | 105.4 | 728.2 | 683.0 | 0.77 | 1.8 | 1.5 | 2.3 |
| T-79 | 110.1 | 496.2 | 448.2 | 0.70 | 4.4 | 2.5 | 2.4 |
| T-80 | 107.1 | 480.1 | 471.2 | 0.68 | 2.4 | 2.6 | 2.6 |
| Parental lines | | | | | | | |
| N-3 | 106.2 | 487.5 | 452.1 | 0.62 | 2.5 | 2.3 | 2.8 |
| I-14 | 97.5 | 379.2 | 363.6 | 0.68 | 1.5 | 1.7 | 1.5 |
| IS-22 | 112.5 | 526.1 | 481.2 | 0.70 | 6.5 | 2.5 | 1.0 |
| Thailand | 116.6 | 403.6 | 386.1 | 0.62 | 7.5 | 3.4 | 2.5 |
| Released varieties | | | | | | | |
| Jawahar-16 | 112.3 | 514.7 | 432.1 | 0.66 | 8.2 | 3.3 | 3.6 |
| Vivek | 111.2 | 568.1 | 394.5 | 0.65 | 7.8 | 3.5 | 3.5 |
| Sanchita | 106.2 | 569.4 | 412.3 | 0.61 | 8.0 | 3.5 | 3.3 |
| Shyama | 107.6 | 489.3 | 345.5 | 0.71 | 7.4 | 3.4 | 3.5 |
| CD at 1% | 3.60 | 21.23 | 19.96 | 0.04 | 0.56 | 0.22 | 0.21 |
| CD at 5% | 2.60 | 10.21 | 10.10 | 0.03 | 0.39 | 0.15 | 0.18 |

TABLE 3

Comparative performance of Rakshit with other elite lines and released and other varieties of opium poppy in a pilot scale trial during 1997–1998.

| Genotypes | Plant height (cm) | Number of capsules/plant | Seed yield (g/8 m$^2$) | Straw yield (g/8 m$^2$) | Morphine content in rated poppy straw (cps) | Downy mildew (0–9 scale) | Damping off (0–4 scale) | Collar rot (0–4 scale) |
|---|---|---|---|---|---|---|---|---|
| T-7 (Rakshit) | 109.0 | 2.0 | 1090.2 | 706.1 | 0.75 | 1.4 | 2.5 | 1.6 |
| T-20-16 | 105.6 | 2.7 | 836.8 | 620.8 | 0.62 | 1.8 | 2.6 | 1.5 |
| T-20-17 | 106.3 | 2.3 | 1016.2 | 677.7 | 0.69 | 1.5 | 3.5 | 1.7 |
| Jawahar-16 | 110.5 | 2.6 | 625.0 | 495.0 | 0.68 | 7.5 | 3.5 | 3.2 |
| Vivek | 110.3 | 2.7 | 732.7 | 566.5 | 0.64 | 7.0 | 2.8 | 2.7 |
| Sanchita | 105.6 | 2.5 | 666.1 | 480.8 | 0.63 | 7.8 | 3.3 | 3.5 |
| Shyama | 105.3 | 2.6 | 568.0 | 509.0 | 0.70 | 7.0 | 3.4 | 2.9 |
| Shubhra | 92.6 | 3.0 | 679.2 | 529.7 | 0.69 | 7.8 | 3.8 | 3.8 |
| CD at 1% | 3.95 | 0.1 | 55.45 | 44.68 | 0.03 | 0.49 | 0.20 | 0.35 |
| CD at 5% | 2.82 | 0.1 | 39.66 | 31.93 | 0.02 | 0.35 | 0.17 | 0.22 |

EXAMPLE 3

Pilot scale trial was again laid out during 1998–99 (RBD, 12 m$^2$ plots, 3 replications row×row=40 cm) with all other released varieties along with the parental (IS-22 & N-3) and elite lines as checks (Table-4). T-7 (Rakshit) recorded 12.59 q/ha seed yield as compared to 9.09 q/ha of Shubhra. Similarly, straw yield of T-7 (Rakshit) was found to be 9.55 q/ha as compared to 7.89 q/ha of Shubhra. Morphine content was found to be comparable in all the entries. However, DM rating of T-7 (Rakshit) was 1.5 (resistant) as compared to 7.7 (highly susceptible) of Shubhra. The disease rating of damping off for T-7 (Rakshit) was 2.0 (tolerant) as compared to 3.7 (highly susceptable)of Shubhra. The disease rating of collar rot for T-7 (Rakshit) was 1.6 (tolerant) as compared to 3.7 (highly susceptible) of Shubhra.

Stability

The variety Rakshit has been found to be stable for all its observed qualitative, quantitative, physiological and chemical characteristics for the last three years. The disease ratings were also found to be consistant and uniform against all the three diseases scored during the last three years of experimentation.

Statement of Distinction

Rakshit is resistant to downy mildew (disease rating 1.2 on 0–9 scale), and tolerant to both damping off and collar rot diseases as compared to all the released varieties (Sanchita, Vivek, Shubhra, Jawahar-16, Shyama & Shweta broad) which are susceptible or highly susceptible to all the above mentioned diseases. Leaf margin of the new variety Rakshit are medium fringed as compared to medium broad leaf margins of Sanchita, Vivek, Jawahar-16, Shyama & Shweta broad. The variety Rakshit also recorded significantly high seed and straw yield (12.59 q and 9.55 q/ha, respectively as compared to 9.09 and 7.89 q/ha in Shubhra).

Figure 3:
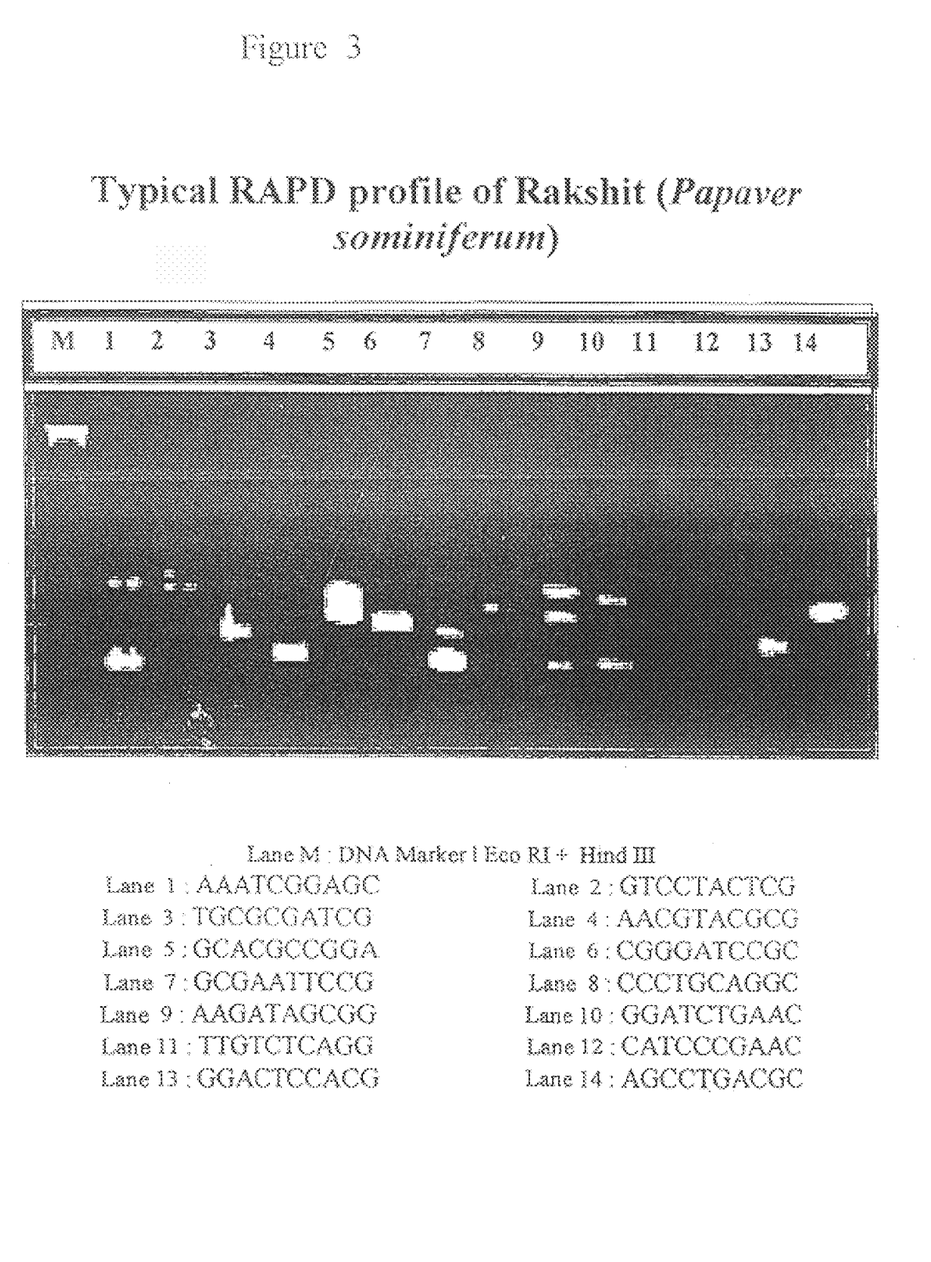
FIG. 3 represents the RAPD analysis of the plant.

A typical RAPD profile of "Rakshit" is represented in FIG. 3 wherein

Lane M: DNA Marker 1 Eco RI+Hind III

Lane 1: AAATCGGAGC (SEQ ID NO: 1)
Lane 2: GTCCTACTCG (SEQ ID NO: 2)
Lane 3: TGCGCGATCG (SEQ ID NO: 3)
Lane 4: AACGTACGCG (SEQ ID NO: 4)
Lane 5: GCACGCCGGA (SEQ ID NO: 5)
Lane 6: CGGGATCCGC (SEQ ID NO: 6)
Lane 7: GCGAATTCCG (SEQ ID NO: 7)
Lane 8: CCCTGCAGGC (SEQ ID NO: 8)
Lane 9: AAGATAGCGG (SEQ ID NO: 9)
Lane 10: GGATCTGAAC (SEQ ID NO: 10)
Lane 11: TTGTCTCAGG (SEQ ID NO: 11)
Lane 12: CATCCCGAAC (SEQ ID NO: 12)
Lane 13: GGACTCCACG (SEQ ID NO: 13)
Lane 14: AGCCTGACGC (SEQ ID NO: 14)

TABLE 4

Comparative performance of Rakshit and other varieties of opium poppy in a pilot scale trial during 1998–1999.

| Genotypes | Plant height (cm) | Days to maturity | Number of capsules/ plant | Seed germination (%) | Seed yield (q/ha) | Oil content in seeds | Straw yield (q/ha) | Morphine content in concentrated poppy straw (cps) | Disease score | | |
|---|---|---|---|---|---|---|---|---|---|---|---|
| | | | | | | | | | Downy mildew (0–9 scale) | Damping off (0–4 scale) | Collar rot (0–scale) |
| T-7 (Rakshit) | 109.3 | 132.0 | 2.0 | 96.7 | 12.5 | 51.6 | 9.55 | 0.77 | 1.4 | 2.0 | 1.6 |
| | 110.5 | 123.1 | 3.2 | 90.3 | 8.6 | 48.2 | 6.02 | 0.70 | 7.5 | 2.5 | 1.0 |
| N-3 | 100.6 | 128.7 | 2.1 | 92.9 | 7.4 | 46.8 | 5.44 | 0.62 | 1.5 | 2.4 | 2.8 |
| T-20-16 | 104.7 | 130.7 | 2.3 | 94.0 | 10.7 | 48.2 | 8.63 | 0.74 | 2.0 | 2.9 | 1.6 |
| T-20-17 | 107.7 | 131.0 | 2.0 | 94.3 | 11.3 | 50.2 | 8.97 | 0.73 | 1.6 | 3.4 | 1.6 |
| Jawahar-16 | 108.1 | 127.4 | 3.0 | 85.0 | 8.1 | 42.1 | 7.1 | 0.65 | 8.0 | 3.5 | 3.2 |
| Vivek | 112.0 | 127.7 | 2.3 | 95.0 | 8.4 | 47.0 | 7.6 | 0.73 | 7.3 | 2.7 | 2.6 |
| Sanchita | 107.7 | 128.7 | 2.0 | 94.0 | 8.4 | 48.3 | 6.9 | 0.74 | 7.7 | 3.1 | 3.6 |
| Shyama | 105.7 | 129.0 | 2.3 | 95.0 | 7.2 | 49.0 | 6.5 | 0.75 | 7.1 | 3.3 | 2.5 |
| Shubhra | 96.0 | 124.3 | 3.0 | 95.0 | 9.1 | 49.5 | 7.9 | 0.77 | 7.7 | 3.7 | 3.7 |
| CD at 1% | 3.6 | 3.7 | 0.20 | 3.9 | 0.9 | 0.9 | 0.5 | 0.05 | 0.67 | 0.21 | 0.30 |
| CD at 5% | 2.6 | 2.6 | 0.15 | 2.8 | 0.6 | 0.7 | 0.4 | 0.03 | 0.48 | 0.15 | 0.21 |

What is claimed is:

1. A disease resistant and high yielding Rakshit variety *Papaver somniferum* having the Accession No. NCPAT17699 (NCIMB 41148) and having the following morphological/agronomic features:

| | |
|---|---|
| Plant height | 106–112 cm |
| Peduncle length | 22–26 cm |
| Peduncle colour | green |
| Seed yield | 12–14 q/ha |
| Straw yield | 9–11 q/ha |
| Days to 50% flowering | 90–100 days |
| Days to maturity | 128–134 days |
| No. of capsules/plant | 1–4 |
| No. of stigmatic rays/capsule | 16–18 |
| Latex colour | dark pink |
| No. of seeds/g | 3350–3390 |
| Seed colour | cream |
| Seed shape | reniform |
| Seed size (L × W) | 1000 × 840–1050 × 855 $\mu$m |
| Leaf area | 127–135 cm$^2$ |
| Pollen fertility | 90–95% |
| Seed germination | 90–98% |
| Oil content in seed | 46–52% |
| Total seed proteins | 28–32% |
| Chlorophyll content | 1.80–1.90 mg/g fresh weight |
| Capsule shape | oblong |
| Capsule surface | waxy |
| Leaf colour | 137B–137 | based on RHS-Royal Horticulture society, London, UK. Cards and resistant to a disease selected from the group consisting of downy mildew caused by *Peronospora arboresces*, damping off caused by *Pythium dissotocum* and collar rot caused by *Rhizoctonia solani*.

2. A plant as claimed in claim 1 wherein the high yielding and disease resistant variety Rakshit of opium poppy has the following disease reactions:

| | Disease | Disease rating | Category | Scale used |
|---|---|---|---|---|
| a) | Downy mildew caused by *Peronospora arborescens* | 1–2 | resistant | (0–9) |
| b) | Damping off caused by *Pythium dissotocum* | 1–2 | tolerant | (0–4) |
| c) | Collar rot caused by *Rhizoctonia solani*. | 1–2 | tolerant | (0–4) |

3. A plant as claimed in claim 1 wherein the straw has a chemical composition comprising:

| | |
|---|---|
| Morphine | 0.65–0.87% |
| Thebaine | 0.03–0.06% |
| Codeine | 0.15–0.19% |
| Papaverine | 0.02–0.10% |
| Narcotine | 0.12–0.17%. |

4. A poppy plant produced from NCPAT17699 seeds having accession number NCPAT17699 (NCIMB 41148).

5. A seed produced by the poppy plant of claim 1.

6. A progeny of the plant of claim 1.

7. A method for development of disease resistant and high yielding variety of poppy, said method comprising the steps of:

a) Screening and selecting parental materials consisting of high yielding genotypes susceptible to the group of diseases consisting of downy mildew caused by *Peronospora arboresces*, damping off caused by *Pythium dissotocum* and collar rot caused by *Rhizoctonia solani*, and highly resistant sources for the most destructive disease downy mildew, from the germplasm under strict epiphytotic conditions.

b) Hybridizing the high yielding genotypes with highly resistant sources in all possible reciprocal combinations to generate an $F_1$ plant, c) Raising $F_2$ generations of all cross combinations and then selfing only the resistant plants in $F_2$ progenies to raise $F_3$ seeds, d) Selecting the highly resistant plants in the $F_3$ generation showing high seed and straw yield, e) Conducting an initial evaluation of 286 $F_4$ plant progenies in row trial and selection of seven promising plant progenies, T-3, T-7, T-16, T-20-16, T-20-17, T-79 and T-80, on the basis of distinctiveness, uniformity, disease rating, seed and straw yield, f) Screening selected plants within the seven plant progenies for damping off, collar rot and downy mildew under epiphytotic conditions in the glasshouse and under natural conditions in the field, g) Purifying selected lines showing high to moderate resistance for all the three diseases in the advanced generation $F_5$ by selfing only the highly resistant and high seed/straw yielding plants, h) Conducting a bench scale evaluation of the purified lines, T-7, T-20-16, T-20-17, T-79 and T-80, against the released variety Shyama as check, RBD 8 m$^2$ plots, 3 replications, r×r=50 cm, i) Conducting a pilot scale evaluation of the purified lines, T-7, T-20-16 and T-20-17 against high yielding released varieties, for two years for the yield and quality traits; and j) Obtaining the disease resistant and high yielding variety of poppy.

8. A method as claimed in claim 7 wherein IS-22 is the female parent and N-3 is the male parent.

9. A method as claimed in claim 7 wherein 0–9 scale disease rating is used for scoring downy mildew reactions under epiphyotic as well as natural field conditions wherein 0–3 is considered resistant (0=no visible disease reactions; 3=less than 20% of the lower leaves covered with disease reactions), 3.1 to 5.0 as moderately resistant or tolerant (3.1=more than 20% disease reactions on lower leaves; 5.0=less than 50% disease reactions on lower leaves), 5.1–7.0 as susceptible (5.1 more than 50% disease reactions on all the leaves and stem; 7.0=less than 75% disease reactions on all the leaves and stem), 7.1 to 9.0 as highly susceptible (7.0 more than 75% disease reactions; 9.0 premature death of the infected plant).

10. A method as claimed in claim 7 wherein 0–4 scale is used for damping off disease reactions under epiphytotic conditions in the glasshouse wherein 0–1 is considered as resistant (0=no visible reactions, 1 very few minute necrotic lesions of limited growth on the roots, no chlorosis), 1.1–2.0 as tolerant or moderately resistant (few necrotic lesions on the roots with chlorotic symptoms only on the lower leaves), 2.1–3.0 as susceptible (many dark brown necroitic lesions on the roots with distinctly visible chlorotic symptoms), 3.1–4.0 as highly susceptible (entire root system with dark brown necrotic and rotting symptoms leading to sudden death of infected seedlings).

11. A method as claimed in claim 7 wherein 0–4 scale disease rating is used for scoring collar rot disease reactions under epiphytotic conditions in the glass house where 0–1 is considered resistant (0=no visible reactions; 1=infection restricted up to 1 cm length on the collar region), 1.1–2.0 as moderately resistant or tolerant (1.1=infection more than 1 cm length on the collar region, 2.0=infection starts spreading in the root and shoot), 2.1–3.0 as susceptible (2.1=infection spreads downwards (root) & upwards (stem) and yellowing of lower leaves, 3.0=pronounced rotting symptoms start appearing at the collar region as well as on the stem of infected plants.), 3.1–4 0 as highly susceptible (3.1=dark brown rotting become more prominent, 4.0=collar region and stem become pulpy resulting in the toppling of infected plants).

* * * * *

SEQUENCE LISTING

```
<160> NUMBER OF SEQ ID NOS: 14

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: : Primer
      for generating random amplified polymorphic DNA profile of claimed
      plant

<400> SEQUENCE: 1
aaatcggagc                                                            10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: : Primer
      for generating random amplified polymorphic DNA profile of claimed
      plant

<400> SEQUENCE: 2
gtcctactcg                                                            10

<210> SEQ ID NO 3
<211> LENGTH: 10
<212> TYPE: DNA
<213> ORGANISM: Artificial Sequence
```

```
-continued

<220> FEATURE:
<223> OTHER INFORMATION: Description of Artificial Sequence: : Primer
      for generating random amplified polymorphic DNA profile of claimed
      plant

<400> SEQUENCE: 3
tgcgcgatcg                                                          10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: : Primer
      for generating random amplified polymorphic DNA profile of claimed
      plant

<400> SEQUENCE: 4
aacgtacgcg                                                          10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: : Primer
      for generating random amplified polymorphic DNA profile of claimed
      plant

<400> SEQUENCE: 5
gcacgccgga                                                          10

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: : Primer
      for generating random amplified polymorphic DNA profile of claimed
      plant

<400> SEQUENCE: 6
cgggatccgc                                                          10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: : Primer
      for generating random amplified polymorphic DNA profile of claimed
      plant

<400> SEQUENCE: 7
gcgaattccg                                                          10

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: : Primer
      for generating random amplified polymorphic DNA profile of claimed
      plant

<400> SEQUENCE: 8
ccctgcaggc                                                          10
```

```
<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: : Primer
      for generating random amplified polymorphic DNA profile of claimed
      plant

<400> SEQUENCE: 9
aagatagcgg                                                          10

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: : Primer
      for generating random amplified polymorphic DNA profile of claimed
      plant

<400> SEQUENCE: 10
ggatctgaac                                                          10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: : Primer
      for generating random amplified polymorphic DNA profile of claimed
      plant

<400> SEQUENCE: 11
ttgtctcagg                                                          10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: : Primer
      for generating random amplified polymorphic DNA profile of claimed
      plant

<400> SEQUENCE: 12
catcccgaac                                                          10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: : Primer
      for generating random amplified polymorphic DNA profile of claimed
      plant

<400> SEQUENCE: 13
ggactccacg                                                          10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: : Primer
      for generating random amplified polymorphic DNA profile of claimed
      plant
```

-continued

```
<400> SEQUENCE: 14
agcctgacgc                                                          10
```